(12) United States Patent
Luo

(10) Patent No.: US 11,351,016 B2
(45) Date of Patent: Jun. 7, 2022

(54) WIRELESS INDUCTION POWER SUPPLY TYPE LIGHT-UP ELECTRIC TOOTHBRUSH

(71) Applicant: Nanchang Smile Technology Co., Ltd., Jiangxi (CN)

(72) Inventor: Huan Luo, Jiangxi (CN)

(73) Assignee: NANCHANG SMILE TECHNOLOGY CO., LTD., Jiangxi (CN)

(*) Notice: Subject to any disclaimer, the term of this patent is extended or adjusted under 35 U.S.C. 154(b) by 56 days.

(21) Appl. No.: 17/103,583

(22) Filed: Nov. 24, 2020

(65) Prior Publication Data

US 2021/0196438 A1 Jul. 1, 2021

(30) Foreign Application Priority Data

Dec. 27, 2019 (CN) .......................... 201922394448.7

(51) Int. Cl.
| | |
|---|---|
| *A61C 17/22* | (2006.01) |
| *H02J 50/10* | (2016.01) |
| *F21V 33/00* | (2006.01) |
| *F21Y 115/10* | (2016.01) |

(52) U.S. Cl.
CPC ........ *A61C 17/224* (2013.01); *F21V 33/0064* (2013.01); *H02J 50/10* (2016.02); *F21Y 2115/10* (2016.08)

(58) Field of Classification Search
CPC .... F21V 33/0064; F21V 33/068; F21V 33/00; F21V 23/00; H02J 50/10; H02J 50/00; A61C 17/224; A61C 2204/002; A61C 17/22; A61C 17/16; F21Y 2115/10; F21Y 2113/10; A61N 2005/0662; A61N 2005/0606; A61N 2005/0651
See application file for complete search history.

(56) References Cited

U.S. PATENT DOCUMENTS

| | | | | |
|---|---|---|---|---|
| 3,145,404 | A * | 8/1964 | Fiedler | H01F 27/40 15/23 |
| 2006/0183071 | A1* | 8/2006 | Hsuch | A61N 5/0603 433/29 |
| 2012/0198635 | A1* | 8/2012 | Hilscher | A61C 17/16 15/22.1 |
| 2014/0199651 | A1* | 7/2014 | Adachi | A61C 17/20 433/27 |
| 2018/0021117 | A1* | 1/2018 | Kitagawa | A61C 17/224 15/22.1 |
| 2020/0179090 | A1* | 6/2020 | Copeland | H02J 7/025 |

* cited by examiner

*Primary Examiner* — Bao Q Truong
(74) *Attorney, Agent, or Firm* — Muncy, Geissler, Olds & Lowe, P.C.

(57) ABSTRACT

Disclosed is a wireless induction power supply type light-up electric toothbrush, including a toothbrush handle body, a main body support, a mainboard, a battery, a motor, a motor sleeve, a waterproof ring, a toothbrush handle cover plate, a toothbrush head cover plate, a toothbrush head rod and a toothbrush head, wherein the toothbrush head is further provided with bristles and a toothbrush head LED panel arranged with several toothbrush head LED lamps. The toothbrush is added with a healthcare function through LED lamps, and the toothbrush head LED lamps are powered up in a wireless manner.

9 Claims, 2 Drawing Sheets

WIRELESS INDUCTION POWER SUPPLY TYPE LIGHT-UP ELECTRIC TOOTHBRUSH

FIELD

The patent belongs to the field of electric toothbrushes, and particularly relates to a wireless induction power supply type light-up electric toothbrush.

BACKGROUND

Through rapid rotation or vibration of a core of an electric motor, a toothbrush head of an electric toothbrush is caused to vibrate at a high frequency, resulting in that toothpaste is suddenly resolved into tiny foam, and deeply clean slits between teeth. Meanwhile, vibration of bristles may promote blood circulation of an oral cavity, and has a massaging effect on gingival tissue. The toothbrush head of the electric toothbrush head on the market at present does not have a light-up function, only have bristles and have no other tooth care functions.

SUMMARY

The patent, focusing on the above problem, aims at providing a wireless induction power supply type light-up toothbrush, a toothbrush head part of which may be lit up so as to achieve the effect of tooth care.

A technical solution of the patent is implemented as follows, the wireless induction power supply type light-up electric toothbrush mainly includes a toothbrush handle body, a main body support, a mainboard, a toothbrush handle battery, a motor, a motor sleeve, a waterproof ring, a toothbrush handle cover plate, a toothbrush head cover plate, a toothbrush head rod and a toothbrush head, wherein the main body support is mounted inside the toothbrush handle body, the main body support is separately provided with the mainboard, the toothbrush handle battery and the motor; the mainboard is provided with a handle button; the motor sleeve includes a handle motor sleeve and a toothbrush head rod motor sleeve, peripheries of a middle part and a lower part of the motor are clad in the handle motor sleeve, and an upper part of the motor is clad in the toothbrush head rod motor sleeve; a mounting groove is provided in a middle-upper part of the handle motor sleeve, and the mounting groove is sequentially connected to a big waterproof ring, an inductance coil holder, a small waterproof ring and the toothbrush handle cover plate from top to bottom in a sleeve mode; the inductance coil holder is provided with a handle emission inductance coil, and the handle emission inductance coil is connected to the mainboard through a lead; the toothbrush head cover plate is upwards provided with a toothbrush head receiving inductance coil, a toothbrush head rod PCB and the toothbrush head rod motor sleeve in sequence; the toothbrush head rod PCB is connected to the toothbrush head receiving inductance coil through a conduction metal sheet or through a welding lead; a toothbrush head support sealing ring is superposed on the toothbrush head rod motor sleeve; an upper part of the toothbrush head rod is provided with the toothbrush head; and the toothbrush head is further provided with bristles and a toothbrush head LED panel, and the toothbrush head LED panel is arranged with several toothbrush head LED lamps.

Further, the wireless induction power supply type light-up electric toothbrush is characterized in that the total number of the toothbrush head LED lamps is set as 6.

Further, the wireless induction power supply type light-up electric toothbrush is characterized in that the toothbrush head LED lamp is one or more arbitrarily combined groups of a purple-light LED lamp, a blue-light LED lamp and a red-light LED lamp.

For the above toothbrush head LED lamp, a light-up band of the purple-light LED lamp is 325 nm-395 nm, and the purple-light LED lamp plays a role in gum relief and gum sensitivity relief; a light-up band of the blue-light LED lamp is 480 nm-520 nm and the blue-light LED lamp plays a role in activation of a whitening factor and a whitening product and achieves a batter whitening effect during use; and a light-up band of the red-light LED lamp is 630 nm-680 nm, and the red-light LED lamp plays a role in sterilization and bacteriostasis, and makes an oral cavity healthier used during tooth brushing.

Further, the wireless induction power supply type light-up electric toothbrush is characterized in that the handle button is provided with a button electroplated ring.

Further, the wireless induction power supply type light-up electric toothbrush is characterized in that the toothbrush head rod PCB is further electrically connected to a toothbrush head rechargeable battery.

Further, the wireless induction power supply type light-up electric toothbrush is characterized in that the toothbrush handle battery is a dry battery or a rechargeable battery.

Further, the wireless induction power supply type light-up electric toothbrush is characterized in that the toothbrush handle battery is a rechargeable battery, in addition, the main body support is further provided with a wireless charging receiving coil, and the wireless charging receiving coil is electrically connected to the toothbrush handle battery.

The wireless charging receiving coil above has an operating frequency range different from that of the handle emission inductance coil and the toothbrush head receiving inductance coil, and no interference is caused therebetween.

An operating principle of the toothbrush is as follows: the toothbrush head of the electric toothbrush of the patent is powered up through wireless induction; and LED lamps with different care effects and different quantities are customized on the toothbrush head LED panels of different toothbrush heads according to requirements of a user, and the different tooth care effects are achieved by changing the toothbrush heads. The toothbrush head receiving inductance coil is mounted in a toothbrush head main rod, and the handle emission inductance coil is mounted at the position, close to a connection position of the toothbrush head, of a top end of the toothbrush handle body. The toothbrush head is powered up by matching and pairing the handle emission inductance coil with the toothbrush head receiving inductance coil.

The beneficial effects of the patent lie in that: 1. according to the patent, the LED lamps with the healthcare effect is designed on the toothbrush head, such that the toothbrush is added with a healthcare function. 2. The matched and paired handle emission inductance coil and the toothbrush head receiving inductance coil are utilized to power up the toothbrush head, which is convenient to replace through wireless charging. 3. The structure is compact and use is convenient.

In the figures: 1. toothbrush handle body, 2. main body support, 3. mainboard, 4. toothbrush handle battery, 5. motor, 6. handle button, 7. button electroplated ring, 8. handle motor sleeve, 9. big waterproof ring, 10. inductance coil holder, 11. small waterproof ring, 12. handle emission inductance coil, 13. toothbrush head cover plate, 15. toothbrush head receiving inductance coil, 16. toothbrush head rod PCB, 19. toothbrush head rod motor sleeve, 20. toothbrush head rod, 21. toothbrush head support sealing ring, 22. toothbrush head, 23. toothbrush head LED panel, 24. toothbrush head LED lamp, 25. toothbrush handle cover plate, 26. wireless charging receiving coil, and 27. toothbrush head rechargeable battery.

DETAILED DESCRIPTION OF THE EMBODIMENTS

Embodiment 1

Figure 1:
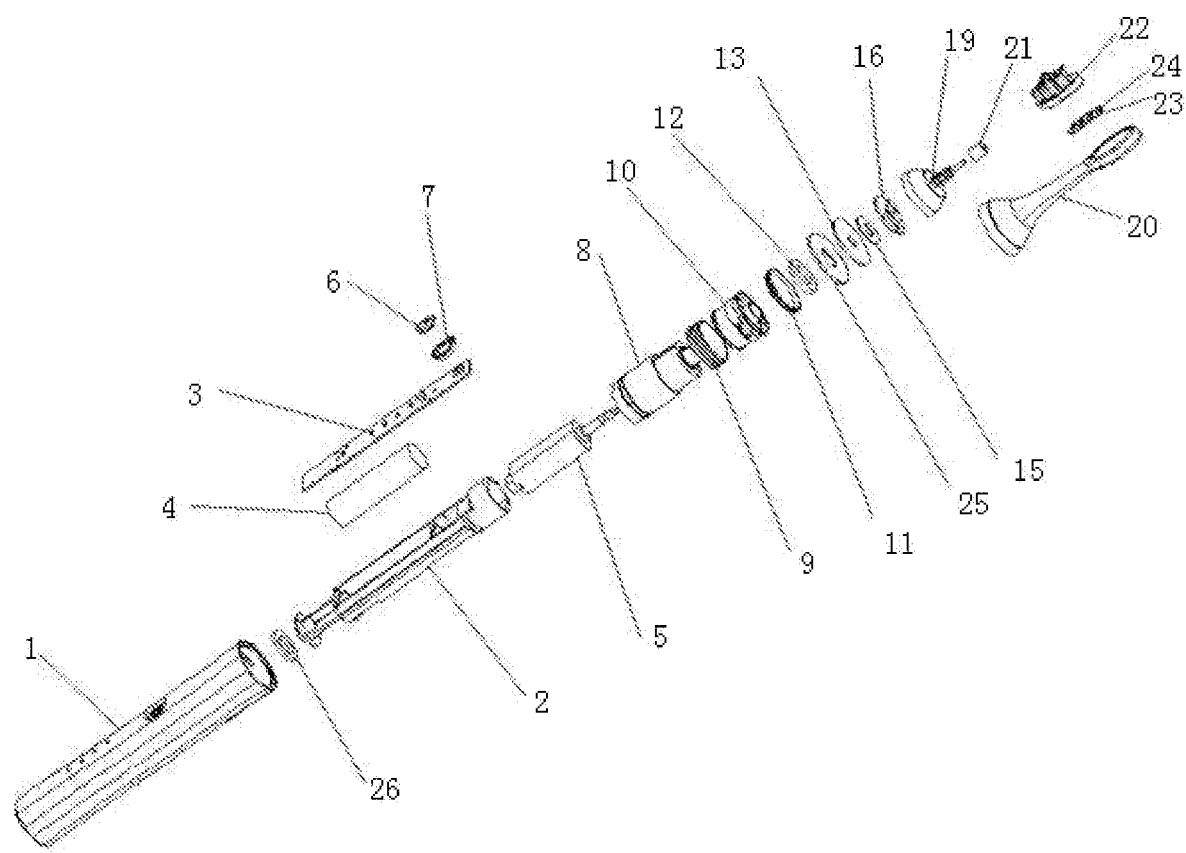
FIG. 1 is a structural exploded diagram of embodiment 1 of the patent.
Figure 2:
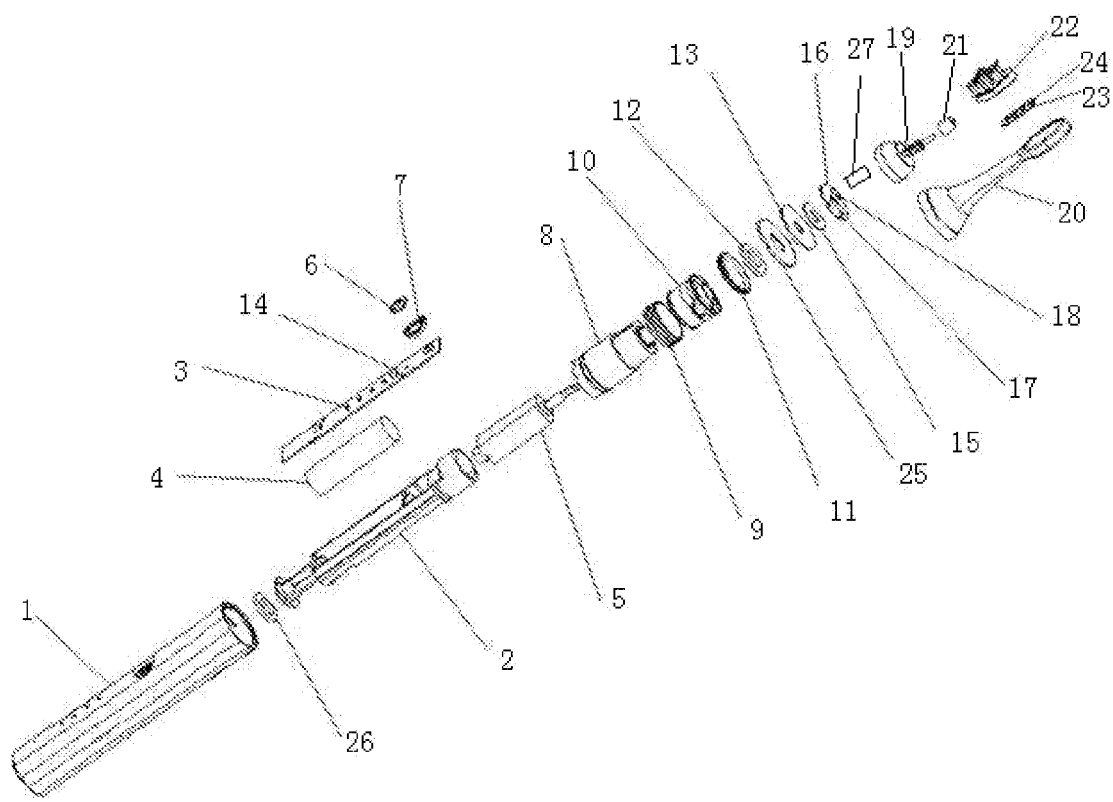
FIG. 2 is a structural exploded diagram of embodiment 2 of the patent.

As shown in FIG. 1 and FIG. 2, a wireless induction power supply type light-up electric toothbrush mainly includes a toothbrush handle body 1, a main body support 2, a mainboard 3, a toothbrush handle battery 4, a motor 5, a motor sleeve, a waterproof ring, a toothbrush handle cover plate 25, a toothbrush head cover plate 13, a toothbrush head rod 20 and a toothbrush head 22, wherein the main body support 2 is mounted inside the toothbrush handle body 1, the main body support 2 is separately provided with the mainboard 3, the toothbrush handle battery 4 and the motor 5; the mainboard 3 is provided with a handle button 6; the motor sleeve comprises a handle motor sleeve 8 and a toothbrush head rod motor sleeve 19, peripheries of a middle part and a lower part of the motor 5 are clad in the handle motor sleeve 8, and an upper part of the motor 5 is clad in the toothbrush head rod motor sleeve 19; a mounting groove is provided in a middle-upper part of the handle motor sleeve 8, and the mounting groove is sequentially connected to a big waterproof ring 9, an inductance coil holder 10, a small waterproof ring 11 and the toothbrush handle cover plate 25 from top to bottom in a sleeve mode; the inductance coil holder 10 is provided with a handle emission inductance coil 12, and the handle emission inductance coil 12 is connected to the mainboard 3 through a lead; the toothbrush head cover plate 13 is upwards provided with a toothbrush head receiving inductance coil 15, a toothbrush head rod PCB 16 and the toothbrush head rod motor sleeve 19 in sequence; the toothbrush head rod PCB 16 is connected to the toothbrush head receiving inductance coil 15 through a conduction metal sheet or through a welding lead; a toothbrush head support sealing ring 21 is superposed on the toothbrush head rod motor sleeve 19; an upper part of the toothbrush head rod 20 is provided with the toothbrush head 22; and the toothbrush head 22 is further provided with bristles and a toothbrush head LED panel 23, and the toothbrush head LED panel 23 is arranged with 6 toothbrush head LED lamps 24.

The total number of the toothbrush head LED lamps 24 is set as 6, and the toothbrush head LED lamp 24 is one or more arbitrarily combined groups of a purple-light LED lamp, a blue-light LED lamp and a red-light LED lamp. For example, all the LED lamps are set as the purple-light LED lamps, or the blue-light LED lamps or the red-light LED lamps. The LED lamps may set as two purple-light LED lamps, two blue-light LED lamps and two red-light LED lamps in an alternative arrangement mode. The LED lamp may be set as a group of 3 purple-light LED lamps and 3 blue-light LED lamps, a group of 3 purple-light LED lamps and 3 red-light LED lamps, etc.

A light-up band of the purple-light LED lamp is 325 nm-395 nm, and the purple-light LED lamp plays a role in gum relief and gum sensitivity relief; a light-up band of the blue-light LED lamp is 480 nm-520 nm and the blue-light LED lamp plays a role in activation of a whitening factor and a whitening product and achieves a batter whitening effect during use; and a light-up band of the red-light LED lamp is 630 nm-680 nm, and the red-light LED lamp plays a role in sterilization and bacteriostasis, and makes an oral cavity healthier used during tooth brushing.

The handle button 6 is provided with the button electroplated ring 7.

The toothbrush handle battery 4 is a dry battery or a rechargeable battery which may be detached and taken out for being charged.

A operating process of the toothbrush is as follows: the handle button 6 is pressed, the motor 5 is started to drive the toothbrush head 22 to operate, the handle button 6 is re-pressed, the handle emission inductance coil 12 is electrified, and conducts, through electromagnetic transduction, electricity to the toothbrush head receiving inductance coil 15, then the toothbrush head rod PCB 16 is powered up by the toothbrush head receiving inductance coil 15, the toothbrush head LED lamp 24 is turned on, the toothbrush head LED lamp 24 may be customized according to requirements of a user, and the user may select different toothbrush heads with LED lamps for tooth care of different effects.

Embodiment 2

A wireless induction power supply light-up electric toothbrush mainly includes a toothbrush handle body 1, a main body support 2, a mainboard 3, a toothbrush handle battery 4, a motor 5, a motor sleeve, a waterproof ring, a toothbrush head cover plate 13, a toothbrush head rod 20 and a toothbrush head 22; and the toothbrush handle battery 4 is a rechargeable battery, in addition, the main body support 2 is further provided with the wireless charging receiving coil 26, and the wireless charging receiving coil 26 is electrically connected to the charging toothbrush handle battery 4. The above wireless charging receiving coil 26 has an operating frequency range different from that of the handle emission inductance coil 12 and the toothbrush head receiving inductance coil 15, and no interference is caused therebetween. The toothbrush head rod PCB 16 is further electrically connected to the toothbrush head rechargeable battery 27, and the rechargeable battery is arranged in the toothbrush head so as to enhance stability of the toothbrush head LED lamp during operation.

Other structures are same as that of embodiment 1.

The embodiment described above is a preferred embodiment of the patent. It shall be noted that for those of ordinary skill in the art, they may make several improvements and polishing on the premise without deviating from a principle of the patent, and these improvements and polishing shall be integrated as falling within the protection scope of the patent.

What is claimed is:

1. A wireless induction power supply type light-up electric toothbrush, mainly comprising a toothbrush handle body, a main body support, a mainboard, a toothbrush handle battery, a motor, a motor sleeve, a waterproof ring, a toothbrush handle cover plate, a toothbrush head cover plate, a toothbrush head rod and a toothbrush head, wherein the main body support is mounted inside the toothbrush handle body, the main body support is separately provided with the mainboard, the toothbrush handle battery and the motor; the mainboard is provided with a handle button; the motor sleeve comprises a handle motor sleeve and a toothbrush head rod motor sleeve, peripheries of a middle part and a lower part of the motor are clad in the handle motor sleeve, and an upper part of the motor is clad in the toothbrush head rod motor sleeve; a mounting groove is provided in a middle-upper part of the handle motor sleeve, and the mounting groove is sequentially connected to a big waterproof ring, an inductance coil holder, a small waterproof ring and the toothbrush handle cover plate from top to bottom in a sleeve mode; the inductance coil holder is provided with a handle emission inductance coil, and the handle emission inductance coil is connected to the mainboard through a lead; the toothbrush head cover plate is upwards provided with a toothbrush head receiving inductance coil, a toothbrush head rod PCB and the toothbrush head rod motor sleeve in sequence; the toothbrush head rod PCB is connected to the toothbrush head receiving inductance coil through a conduction metal sheet or through a welding lead; a toothbrush head support sealing ring is superposed on the toothbrush head rod motor sleeve; an upper part of the toothbrush head rod is provided with the toothbrush head; and the toothbrush head is further provided with bristles and a toothbrush head LED panel, and the toothbrush head LED panel is arranged with several toothbrush head LED lamps.

2. The wireless induction power supply type light-up electric toothbrush according to claim 1, wherein the total number of the toothbrush head LED lamps is set as 6.

3. The wireless induction power supply type light-up electric toothbrush according to claim 1, wherein the toothbrush head LED lamp is one or more arbitrarily combined groups of a purple-light LED lamp, a blue-light LED lamp and a red-light LED lamp.

4. The wireless induction power supply type light-up electric toothbrush according to claim 3, wherein a light-up band of the purple-light LED lamp is 325 nm-395 nm; a light-up band of the blue-light LED lamp is 480 nm-520 nm; and a light-up band of the red-light LED lamp is 630 nm-680 nm.

5. The wireless induction power supply type light-up electric toothbrush according to claim 1, wherein the handle button is provided with a button electroplated ring.

6. The wireless induction power supply type light-up electric toothbrush according to claim 1, wherein the toothbrush head rod PCB is further electrically connected to a toothbrush head rechargeable battery.

7. The wireless induction power supply type light-up electric toothbrush according to claim 1, wherein the toothbrush handle battery is a dry battery or a rechargeable battery.

8. The wireless induction power supply type light-up electric toothbrush according to claim 1, wherein the toothbrush handle battery is a rechargeable battery, in addition, the main body support is further provided with a wireless charging receiving coil, and the wireless charging receiving coil is electrically connected to the toothbrush handle battery.

9. The wireless induction power supply type light-up electric toothbrush according to claim 8, wherein the wireless charging receiving coil has an operating frequency range different from that of the handle emission inductance coil and the toothbrush head receiving inductance coil.

\* \* \* \* \*